United States Patent [19]

Le Boeuf

[11] 4,309,592
[45] Jan. 5, 1982

[54] ELECTRIC HEATING DEVICE FOR HEATING STERILIZED FLUIDS, SUCH AS BLOOD

[75] Inventor: Guy Le Boeuf, 9 rue Aristide Briand, Cormeilles en Parisis, France, 95240

[73] Assignee: Guy Le Boeuf, Cormeilles en Parisis, France

[21] Appl. No.: 6,696

[22] Filed: Jan. 25, 1979

[51] Int. Cl.³ .................. H05B 1/02; F24H 1/12; A61M 5/14; B67D 5/62
[52] U.S. Cl. .................. 219/299; 128/214 A; 128/214 D; 128/272; 128/399; 165/46; 219/301; 219/302; 219/305; 219/308; 219/328; 219/330; 219/497; 219/506; 222/146 HE
[58] Field of Search .............. 219/296, 298, 299, 301, 219/302, 305, 308, 309, 328, 497–499, 506; 128/214 A, 214 D, 272, 399, DIG. 24; 165/46; 222/146 HE, 146 H

[56] References Cited

U.S. PATENT DOCUMENTS

| | | | |
|---|---|---|---|
| 3,140,716 | 7/1964 | Harrison et al. | 128/214 A |
| 3,475,590 | 10/1969 | Pins | 219/302 |
| 3,485,245 | 12/1969 | Lahr et al. | 165/46 X |
| 3,590,215 | 6/1971 | Anderson et al. | 165/46 X |
| 3,612,059 | 10/1971 | Ersek | 165/46 X |
| 4,019,020 | 4/1977 | Bilbee et al. | 219/302 |
| 4,167,663 | 9/1979 | Granzow | 219/214 A |

FOREIGN PATENT DOCUMENTS

| | | | |
|---|---|---|---|
| 2530928 | 1/1977 | Fed. Rep. of Germany | 219/296 |
| 2619438 | 11/1977 | Fed. Rep. of Germany | 219/302 |

*Primary Examiner*—A. Bartis
*Attorney, Agent, or Firm*—Sprung, Felfe, Horn, Lynch & Kramer

[57] ABSTRACT

A device for heating blood for transfusion is disclosed which has two vertically disposed opposed electrical heating plates which engage the opposite faces of a flat bag of flexible plastic material delimitating a fluid path therethrough which has a width progressively increasing from a lower inlet pipe for connection to a blood supply to an elongated single rectilinear main portion of uniform width and progressively decreasing from the elongated main portion toward an upper outlet pipe for connection to injection means. A flow restricting means is disposed therein on an intermediate level between the inlet pipe and the main portion of the fluid path to restrict the travel of fluid introduced by the inlet pipe and produce a substantially homogeneous flow all across the main portion of the fluid path. The heating plates include heat radiating fins or corrugations to reduce thermal inertia as the rate of blood flow changes. The electric heating means of each plate is so distributed that the heating power gradually decreases from the bottom to the top of each plate.

10 Claims, 6 Drawing Figures

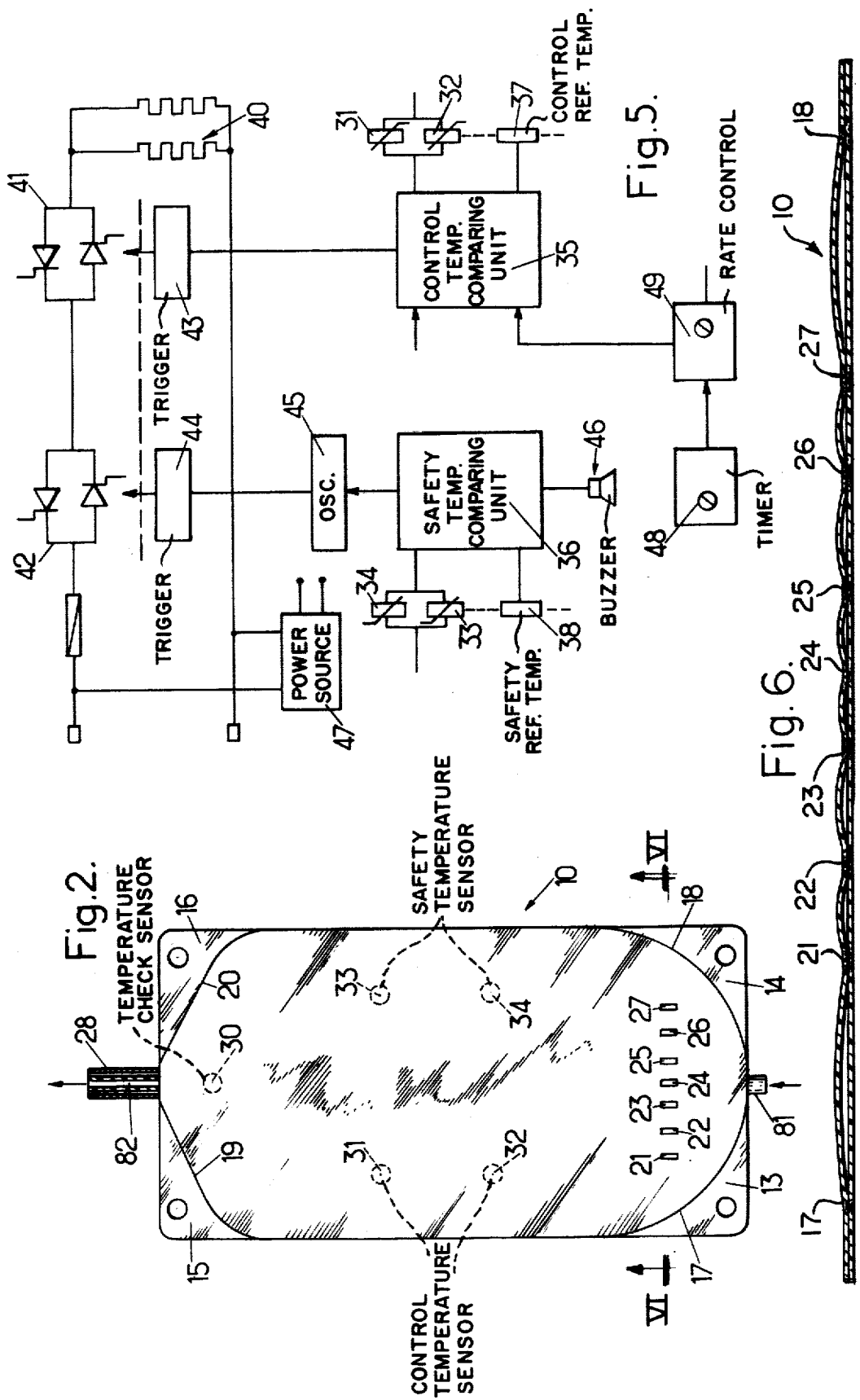

ELECTRIC HEATING DEVICE FOR HEATING STERILIZED FLUIDS, SUCH AS BLOOD

The invention relates to a device for heating a sterilized fluid, such as blood, and other fluids which are to be administrated to a patient.

For injecting blood in a transfusion equipment commonly used, it is known to direct the blood towards the injection needle through a plastic bag which is hung up above the patient. It is also known to heat the blood while it is being circulated through a flexible pipe formed as a coil.

The object of the invention is to provide an improved heating device for fluids such as blood, which can be used on the circuit of a fluid to be injected to a patient in an apparatus such as a transfusion apparatus.

A more specific object of the invention is to provide a bag for blood, which can be included in a blood heating device, and to avoid hemolysis of the blood.

A further object of the invention is to provide a heating apparatus comprising two heating plates on one and the other sides of a bag through which the blood can be circulated.

A further object of the invention is to provide regulating means for controlling the temperature of the blood circulated through a bag between two heating plates in such a way to avoid any such high temperatures or any such quick rise of the temperature which would induce hemolysis of the blood or be otherwise detrimental to it.

Further objects of the invention are to provide a blood heating device permitting without hemolysis to increase the temperature of the blood from the storing temperature of 4° C. to the body temperature of 37° C., even when high amounts of blood must be heated, for instance when the device must supply flow rates of more than 12 liters per hour of warm blood, to increase the thermal yield of the device, to avoid the introduction of air bubbles in the blood to be injected, to heat the blood uniformly on a large surface where the blood is distributed inside the device, to avoid any sudden changes of the temperatures both from one point to another and from one moment to another, and to reduce substantially the pressure drop encountered by the blood due to the heating device compared to known devices.

In a preferred embodiment, the device according to the invention for heating blood for transfusion comprises two electric heating plates enclosing a removable flat bag on two opposite faces thereof, said flat bag being made of a flexible plastic material, and temperature regulating means for controlling an electric current supplied to the heating plates according to the temperature of the blood in the bag.

The bag for the blood has a width progressively increasing from a lower inlet pipe for connection to blood supply means to an elongated main portion of uniform width and progressively decreasing from said elongated main portion towards an upper outlet pipe for connection to injection means. In the lower portion, at a level intermediate between the opening of the inlet pipe and the main portion, the bag comprises restricting means provided so as to hinder the circulation of the fluid on definite points of the section separated by open intervals. Such restricting means may be formed by welds connecting together the walls of the two opposite faces across the inside space of the bag.

The heating plates or heating elements are each provided with electric resistors which are distributed along the elongated main portion of the blood bag so that the heating power transferred to the blood is higher at the beginning of the travel of the blood between the heating elements and lower at the end of this travel. However, the distribution of the heating power is such that the temperature of the plates progressively rises from the inlet to the outlet of the bag when cold blood is admitted through the bag. Generally each element comprises several resistors, for instance from three to twelve resistors all placed transversally to the fluid travel, i.e. horizontally, and these resistors may be each identical but with the lower ones nearer to each other than the upper ones. Furthermore, the resistors are enclosed between an inside flat face adapted to contact the bag and an outside face comprising heat radiating means such as ribs or corrugations exposed to the ambient air. These heat radiating means lead to a substantial reduction of the effects of the thermal inertia which would injure the blood when in the course of a transfusion the blood flow rate is reduced from a high value to a low value.

The temperature regulating means comprise temperature sensors which are mounted in at least one of the heating elements so that they are in good heat conducting connection with the blood bag or with this bag and also with the mass of the heating element. Admitting the electric current to the resistors is controlled on the all and nothing mode so as to keep the temperature measured by the sensors between a maximum and a minimum. The temperature used for this control may be the mean value from two sensors provided at two different levels of the device. On another hand, it is preferred to provide the temperature regulating means with two control circuits, the one for normal operation, the other for safety.

The invention will now be described in details in connection with the appended drawings. On these drawings:

FIG. 2 shows the specific shape of the blood bag;

FIG. 5 is a diagram of the temperature regulating circuits; and

FIG. 6 is a sectional view of the blood bag of FIG. 2 taken along line VI—VI of FIG. 2.

Figure 1:
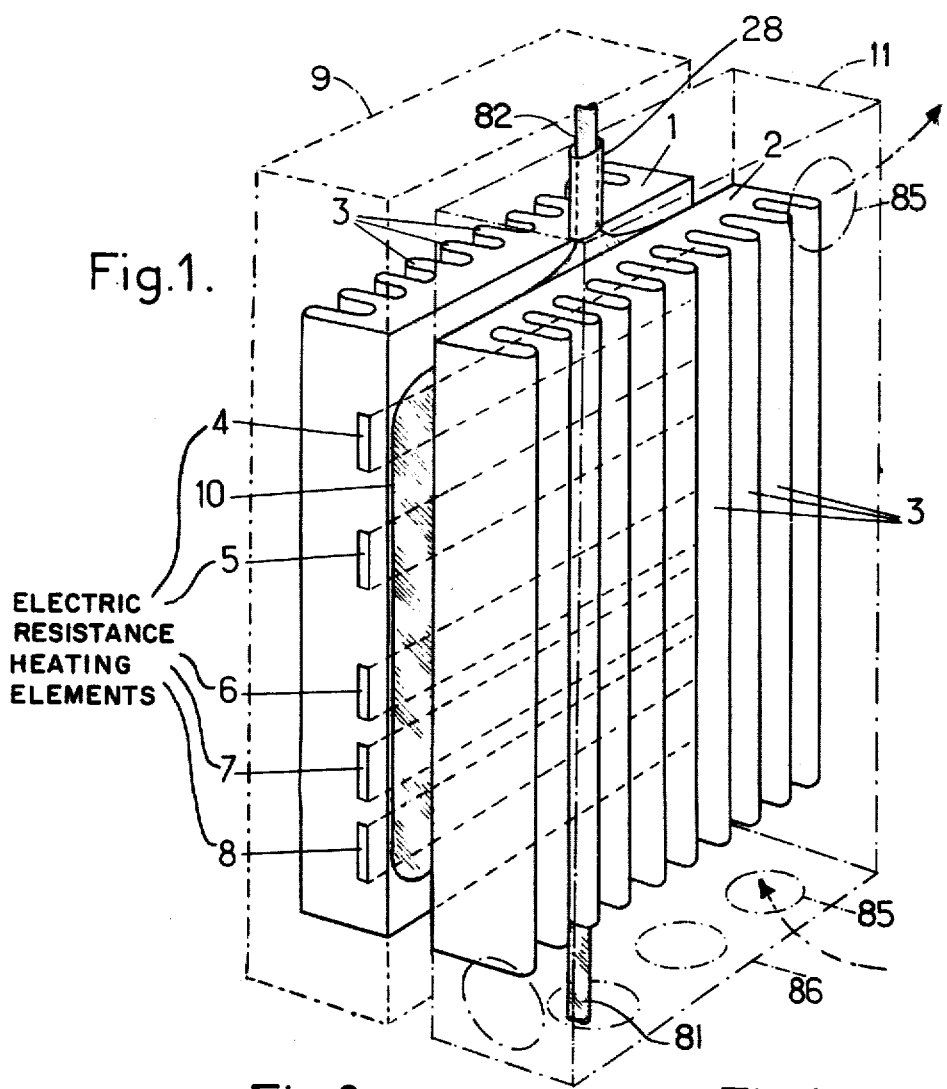
FIG. 1 is a schematic general view of the device, showing the relative disposition of the blood bag and the heating elements.

According to FIG. 1, a device for use for heating transfusion blood to be injected to a patient comprises essentially a blood bag 10 and two heating elements 1 and 2 made of aluminum plates containing isolated resistors embedded therein, said resistors being connected in series or in parallel to an electric current supply source which has not been shown on the drawing.

As shown on FIG. 2, the blood bag 10 is a thin flat bag made of two sheets of a flexible plastic material such as polyvinylchloride welded together. The thickness of the bag may be for instance from 2 to 4 millimeters and the thickness of the plastic sheets constituting the walls may be from 0.10 to 0.25 mm. Each sheet has a rectangular shape and may have for instance a size of 165 mm × 320 mm.

The rectangular plastic sheets are welded together at all four corners 13, 14, 15, 16, and the welds end along curved lines 17, 18, 19, 20, which delimitate an internal space comprising three portions as described hereinafter. In position for use the blood bag is vertically elongated and the blood circulates upwards through it. The bag therefore comprises an inlet pipe 81 in the middle of its bottom side and an outlet pipe 82 in the middle of its top side, both pipes extending axially from the bag. The inlet pipe 81 is connected to a blood supply tank not shown, and the outlet pipe 82 is connected to an injection needle, also not shown. Along the travel of the blood the fluid flow path of bag 10 comprises a lower portion, the width of which is progressively increasing from the opening of the inlet pipe 81 along the curved lines 17, 18, a rectilinear main elongated portion having a uniform width corresponding to the larger passage way for the blood in the internal space of the bag, and an upper portion the width of which progressively decreases from the main portion towards the opening of the outlet pipe 82 along the curved lines 19 and 20. The outlet pipe 82 is surrounded by a tube 28 of larger diameter which retains some still air about the pipe, thereby providing heat insulation and reducing the heat losses, especially when the blood flow rate is low.

At an intermediate level within the lower portion of the bag the sheets constituting the walls of the bag on the opposite faces are welded together across the internal space at definite spaced points. The blood is thus compelled to flow through the intervals between the successive welds. Three welds, 23, 24, 25, have been provided in the center part of the bag and on either sides two intermediate welds 22 and 26 and two end welds 21 and 27. The intervals between the center welds 23, 24, 25, are relatively small, for instance 4 mm, whereas the intervals between the lateral center welds 23, 25, and the intermediate welds 22 and 26 respectively are larger, for instance 8 mm, and the intervals between the intermediate welds and the end welds 21 and 27 respectively are still larger, for instance 17 mm. The width of the welds themselves may be typically of 1-2 mm.

The specific shape of the bag shown on FIG. 2 ensures that when the blood flow rate is high the blood will not ascend in the middle part of the bag faster than on the lateral parts. By restricting the open passage way for the fluid more in the center part than on the sides, the welds 21-27, also act to avoid any discrepancy between the rates of flow of the blood all across the width of the bag. An homogeneous flow rate is obtained above the level of the welds.

The heating plates 1 and 2 are contained within two hingedly connected parts 9 and 11 of a casing so as to removably enclose the bag 10. However, neither the casing nor the hinge connection has been detailed on FIG. 1. This figure shows that when they are in the closed position the heating plates 1 and 2 are in contact with the two opposite faces of the bag 10 by flat inside faces of the plates. On the contrary, each plate comprises on its outside face corrugations which have been represented as vertical ribs or fins 3, the purpose of which is to promote heat exchange with the ambient air circulating along them. Openings 85 are provided through the walls 86 of the casing at its bottom and at its top to enable the atmospheric air to pass through it along the outside face of the heating plates. The size of the plates may be typically 300 cm × 19 cm × 0.4 cm and the ribs may be 15 mm high.

The fraction of the total heating power from the plates which is effectively used to heat the blood may be for instance of 90% when the blood flow rate is of 18 liters per hour, but if the flow rate is decreased down to 0.18 liter per hour the temperature increases and the heating electric current is cut off by the regulating circuits. There still occurs some heating of the blood circulating through the bag due to the heat accumulated in the heating plates but about 10% only of this heat is effective to heat the blood while the remaining 90% are used to heat the ambient air by radiation. This results in avoiding a sudden increase of the temperature of the blood each time the flow rate is abruptly reduced during a transfusion.

A number of heating resistors 4, 5, 6, 7, 8, have been shown on FIG. 1. They are insulated and embedded inside the plate 1 and of course the plate 2 is similarly provided with resistors. The resistance values and the distribution of the resistors along the height of the plates are determined so as to obtain a heating power gradually decreasing from the bottom to the top of the device when they are supplied with the same electric current. This is especially useful for high flow rates. The purpose is to supply the higher heating power required in the lower parts of the device because of the higher difference between the temperatures of the blood and heating plates.

One of the heating plates is provided with thermistors for sensing the temperature on the inside face of the plate. These thermistors or sensors are in the positions illustrated by the reference numbers 30, 31, 32, 33, 34, on FIG. 2. The purpose of the checking sensor 30 is to measure the actual temperature of the blood in the vicinity of the outlet opening of the bag. The sensors 31, 32, are connected to a normal controlling circuit of the regulating means and the sensors 33, 34, are connected to a safety controlling circuit. The sensors 31 to 34 are mounted so as to measure a temperature intermediate that of the blood in the bag and that of the plate. The sensors 31 and 33, one of each pair, are at a level higher than the level of the other sensors 32, 34. The two sensors of each pair are connected in parallel to the associated temperature control circuit, so that the temperature regulated is a mean temperature between those measured at the two levels.

Figures 3, 4:
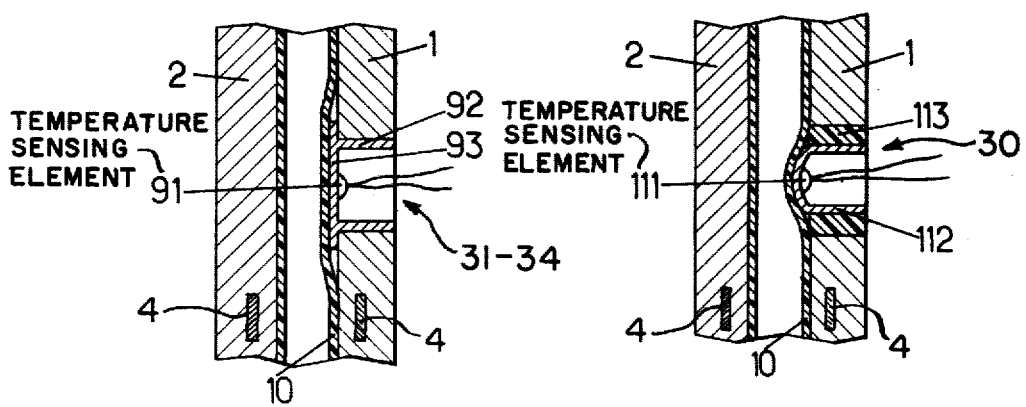
FIG. 3 shows how a sensor of the regulating means is mounted in one of the heating elements.
FIG. 4 shows how a checking temperature sensor is mounted in one of the heating elements.

The temperature sensors 31 to 34 are mounted in the plate 1 as shown on FIG. 3. The sensing element 91 is supported by a metal holder comprising a cylindrical ring 92 and a disc plate 93 protruding from the plate. The cylindrical ring 92 is in good thermal contact with the heating plate 1 whereas the disc plate 93 is in good thermal contact with the wall of the bag 10 which is slightly deformed along it and pressed against it by the blood pressure. In operation, when the heating plates are first being heated up before blood is supplied to the bag, the sensors 31 to 34 give an indication of the temperature which only depends on the temperature of the plate. All the sensors are then at the same temperature because the heating plates are made of a metal which is a good heat conductor. As soon as blood arrives in the bag at the level of the lower sensors 32 and 34, these sensors indicate a lower temperature due to the low temperature of the blood. The two sensors in each pair are so connected to the associated temperature regulating circuit that the electric current is supplied to the resistors whenever any of the sensors indicates a temperature lower than a given minimum, whereas the electric current supply is cut off when any of these sensors indicates a temperature higher than a given maximum. If the range from minimum to maximum is typically 37° C.±0.1° C. or 40° C.±0.1° C., this ensures that the temperature of the blood never increases enough to encounter hemolysis, even though its temperature at the inlet of the bag may vary, for instance from 4° C. to 11° C. or even more, according to the ambient temperature and the blood flow rate in the pipe leading the blood to the device.

The checking temperature sensor 30 is mounted in the plate 1 as shown on FIG. 4. The sensing element 111 is supported by a holder 112 which is fixed inside the plate and protrudes from its inside face against the bag 10 similarly to the other sensors, but the cylindrical ring of the holder 112 is separated from the metal of the plate by a heat insulating ring 113. Therefore, the sensor is only sensible to the temperature of the bag 10, which is equal to the temperature of the blood in the bag, except that when the bag is empty this temperature is substantially equal to that of the plate. Whereas the temperature is measured by sensor 30 near the outlet, it should be noted that in operation, a temperature gradient is established between the inlet and the outlet.

The regulating circuits will now be explained with reference to FIG. 5. The resistors of the heating plates have been represented on the diagram, with a reference number 40, as supplied with an electric current from the mains through two switching circuits in series 41 and 42, each comprising a pair of thyristors, where the two thyristors are mounted in parallel and in reverse positions (head to tail). In each switching device the pair of thyristors may be replaced by a single triac. The switching devices 41 and 42 are controlled by two different electronic circuits through their respective triggering circuits 43 and 44. The current for the continuous electronic components of the device is supplied with a low voltage current (6 or 12 volts) by an auxiliary power source 47 comprising an insulated voltage reducer.

The temperature sensors of the heat plate 1 have been shown on FIG. 5 as thermistors 31, 32, 33, 34. The regulating circuit efficient in normal operation comprises the pair of the two thermistors 31, 32, mounted in parallel, a comparing unit 35 which compares the temperature measured by thermistors 31 and 32 to a reference temperature set at 37 and controls the switching circuit 41 through its associated triggering circuit 43 so that this switching circuit is conductive for the current flow when the temperature measured is lower than the reference temperature, whereas it is blocked to stop the current flow as soon as the temperature measured becomes higher than the reference temperature. The reference temperature set at 37 may be, for instance, 37° C.

The second temperature regulating circuit is similar to the first one as regards the thermistors 33, 34, and the comparing circuit 36 which controls the switching circuit 42 through the associated triggering circuit 44 according to the value of the temperature measured compared to a reference temperature set at 38. The reference temperature is higher in this circuit. It may be, for instance, 40° C.

But in normal operation and as long as the temperature of the plate does not reach 40° C., only the first regulating circuit is used. In order that the second circuit does not interfere with the first one, and the switching circuit 42 remains conductive for the current flow all the time, an oscillator 45 is provided on the line from the comparing unit 36 to the triggering circuit 44. It delivers to the triggering circuit a signal at high frequency, for instance 100 KHz. Only in case of failure of the first regulating circuit will the temperature increase above 37° C. and the second circuit will then become effective to stop the oscillator if the temperature reaches 40° C. and control the switching circuit 42.

A buzzer is provided at 46 to indicate that the temperature of the plates has reached the reference temperature set at 38 on the safety circuit and thus warn the user that the normal circuit requires some maintainance.

When starting to use the device described, the heating plates are first warmed up to the reference temperature (37° C.) before blood is introduced in the bag. It may then be desirable to slow down the temperature rise so as to avoid any increase of the temperature of the plates above 40° C. after the current flow has been stopped, due to the normal low thermal inertia. For this purpose, the regulating circuits of FIG. 5 comprise a timer 48 which can set a time from 1 to 3 minutes during which the rate control circuit 49 is effective to periodically start and stop the flow of current through the resistors 40 until the reference temperature set at 37 is reached. The respective time periods during which the current flow is off or on may be varied, for instance from 2 seconds on and 8 seconds off to 5 seconds on and 5 seconds off.

However, it should be understood the above embodiments are only non limiting examples of the possible embodiments of the present invention.

I claim:

1. A device for heating blood for transfusion, comprising two vertically disposed opposed electric heating plates engaging the opposite faces of a flat bag for supplying heat thereto and temperature regulating means for controlling an electric current supplied to the heating plates according to the temperature of the bag, said flat bag being made of a flexible plastic material and delimitating a fluid path through said bag which has a width progressively increasing from a lower inlet pipe for connection to a blood supply means to a single rectilinear elongated main portion of uniform width and progressively decreasing from said elongated main portion towards an upper outlet pipe for connection to injection means, said bag comprising flow restricting means at an intermediate level between the inlet pipe and the main portion of the fluid path, restricting the travel of fluid introduced by said inlet pipe and producing a substantially homogeneous flow rate all across the main portion of the fluid path.

2. A device according to claim 1, wherein each of said heating plates comprises an inside flat face adapted to contact said bag and an outside face comprising heat radiating means.

3. A device according to claim 2, wherein each of said heating plates includes electric resistors embedded therein at distances from each other which gradually increase along the travel of a fluid in said bag from said inlet pipe to said outlet pipe.

4. A device according to claim 2, wherein said temperature regulating means comprises two control circuits, one for normal operation and the other for safety operation, controlling the heating power admitted to the heating plates to maintain the temperature of the bag below the respective reference temperatures of the respective control circuits, the reference temperature being lower for the one of said circuits used in normal operation than for the other one of said circuits used in safety operation.

5. A device according to claim 4, wherein each of said control circuits comprises a respective switching circuit controlled thereby on a line supplying the plates with an electric heating current and the safety circuit comprises means to render a control of the switching circuit by said safety circuit ineffective as long as the normal circuit is effective to maintain the temperature of the plates beneath the corresponding reference temperature.

6. A device according to claim 1 wherein said flat bag is made of two sheets of flexible plastic material welded together at spaced points distributed on a line at an intermediate level between said inlet pipe and said main portion whereby said welds connect the walls of the two opposite faces across the inside space of the bag, whereby said welds act as said flow restricting means to hinder the circulation of fluid through said bag and produce a substantially homogeneous flow rate all across the width of the main portion of the fluid path.

7. A device for heating blood for transfusion, comprising two vertically disposed opposed electric heating plates engaging the opposite faces of a flat bag for supplying heat thereto, and temperature regulating means for controlling an electric current supplied to the heating plates according to the temperature of the bag, wherein each of said heating plates is enclosed, at least on its outside face, by a casing element having upper and lower openings for the circulation of ambient air along said radiating means, said radiating means comprising corrugations on at least one heating plate and wherein said flat bag is made of a flexible plastic material and delimitates a fluid path through said bag which has a width progressively increasing from a lower inlet pipe for connection to blood supply means to a single rectilinear elongated main portion of uniform width and progressively decreasing from said elongated main portion towards an upper outlet pipe for connection to injection means.

8. A device according to claim 7 wherein each of said heating plates includes electric resistors embedded therein at distances from each other which gradually increase along said path from said inlet pipe to said outlet pipe.

9. A bag for receiving blood circulated through a blood heating device, said bag being made of two sheets of flexible plastic material welded together to form a flat bag, and delimitating a fluid path which has a width progressively increasing from a lower inlet pipe to a single rectilinear elongated main portion of uniform width and progressively decreasing from said elongated main portion towards an upper outlet pipe, said sheets being welded together at spaced points distributed on a line at an intermediate level between said inlet pipe and said main portion, whereby said welds act as restricting means to hinder fluid circulation through said bag and produce a substantially homogeneous flow rate all across the width of the main portion of the fluid bag.

10. A device for heating blood for transfusion, comprising two vertically disposed opposed electric heating plates engaging the opposite faces of a flat bag for supplying heat thereto, and temperature regulating means for controlling an electric current supplied to the heating plates according to the temperature of the bag, wherein said flat bag is made of a flexible plastic material and delimitates a fluid path through said bag which has a width progressively increasing from a lower inlet pipe for connection to blood supply means to a single rectilinear elongated main portion of uniform width and progressively decreasing from said elongated main portion towards an upper outlet portion for connection to injection means and wherein said temperature regulating means comprise two pairs of temperature sensors in thermal conductive connection with both the bag and a plate, the temperature sensors in each pair being located at two different levels in the device.

* * * * *